United States Patent
Tabard-Cossa et al.

(10) Patent No.: US 11,198,946 B2
(45) Date of Patent: *Dec. 14, 2021

(54) INTEGRATING NANOPORE SENSORS WITHIN MICROFLUIDIC CHANNEL ARRAYS USING CONTROLLED BREAKDOWN

(71) Applicant: THE UNIVERSITY OF OTTAWA, Ottawa (CA)

(72) Inventors: Vincent Tabard-Cossa, Québec (CA); Michel Godin, Ottawa (CA); Radin Tahvildari, Ottawa (CA); Eric Beamish, Ottawa (CA)

(73) Assignee: THE UNIVERSITY OF OTTAWA, Ottawa (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/907,897

(22) Filed: Jun. 22, 2020

(65) Prior Publication Data

US 2020/0325593 A1  Oct. 15, 2020

Related U.S. Application Data

(63) Continuation of application No. 15/537,673, filed as application No. PCT/IB2015/059799 on Dec. 18, 2015, now Pat. No. 10,718,064.

(Continued)

(51) Int. Cl.
*C25F 7/00* (2006.01)
*C25F 3/14* (2006.01)
(Continued)

(52) U.S. Cl.
CPC .............. *C25F 7/00* (2013.01); *B81B 3/0018* (2013.01); *C25F 3/14* (2013.01); *G01N 27/40* (2013.01);
(Continued)

(58) Field of Classification Search
CPC .......... C25F 3/14; C25F 7/00; B01D 2325/02; G01N 27/40
See application file for complete search history.

(56) References Cited

U.S. PATENT DOCUMENTS

| | | |
|---|---|---|
| 2002/0127144 A1 | 9/2002 | Mehta |
| 2005/0072689 A1 | 4/2005 | Spohr et al. |
| 2005/0102721 A1 | 5/2005 | Barth |

(Continued)

FOREIGN PATENT DOCUMENTS

| | | |
|---|---|---|
| EP | 1526109 A2 | 4/2005 |
| JP | 2004510980 A | 4/2004 |
| WO | WO-2002008748 A2 | 1/2002 |

(Continued)

OTHER PUBLICATIONS

International Search Report and Written Opinion of the International Searching Authority, issued in PCT/IB2015/059799, dated Mar. 16, 2016; ISA/CA.

(Continued)

*Primary Examiner* — Nicholas A Smith
(74) *Attorney, Agent, or Firm* — Harness, Dickey & Pierce, P.L.C.

(57) ABSTRACT

Nanopore arrays are fabricated by controlled breakdown in solid-state membranes integrated within polydimethylsiloxane (PDMS) microfluidic devices. This technique enables the scalable production of independently addressable nanopores. By confining the electric field within the microfluidic architecture, nanopore fabrication is precisely localized and electrical noise is significantly reduced during sensing.

21 Claims, 15 Drawing Sheets

Related U.S. Application Data

(60) Provisional application No. 62/094,669, filed on Dec. 19, 2014.

(51) Int. Cl.
  *G01N 33/487* (2006.01)
  *B81B 3/00* (2006.01)
  *G01N 27/40* (2006.01)
  *G01N 27/447* (2006.01)

(52) U.S. Cl.
  CPC .......... *G01N 27/44791* (2013.01); *G01N 33/48721* (2013.01); *B01D 2325/02* (2013.01)

(56) References Cited

U.S. PATENT DOCUMENTS

| | | |
|---|---|---|
| 2013/0092541 A1 | 4/2013 | Drndic et al. |
| 2013/0333721 A1 | 12/2013 | Balagurusamy |
| 2014/0179909 A1 | 6/2014 | O'Halloran et al. |
| 2015/0299784 A1 | 10/2015 | Fan et al. |

FOREIGN PATENT DOCUMENTS

| | | |
|---|---|---|
| WO | WO-2013167955 A1 | 11/2013 |
| WO | WO-2014105246 A2 | 7/2014 |
| WO | WO-2014144818 A2 | 9/2014 |

OTHER PUBLICATIONS

H. Kwok et al. Nanopore Fabrication by Controlled Dielectric Breakdown, PLOS ONE, vol. 9, No. 3 (Mar. 21, 2014).
European Search Report, issued in EP 15869455.4 dated Jul. 9, 2018.

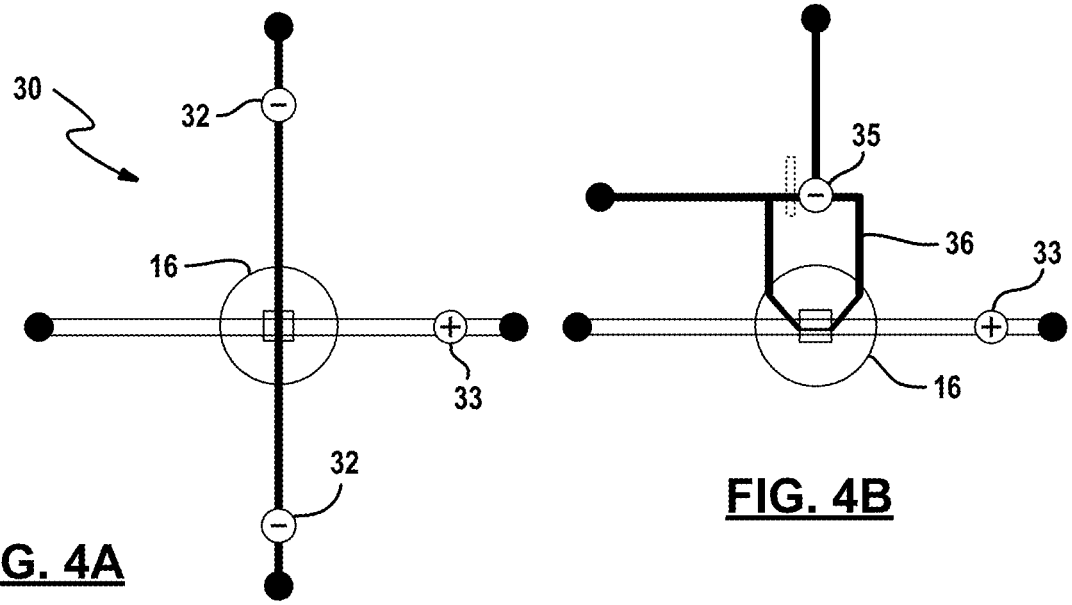
FIG. 4A
FIG. 4B
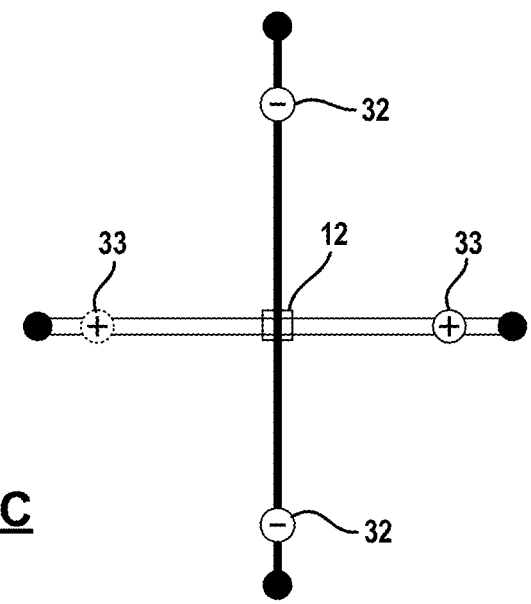
FIG. 4C

INTEGRATING NANOPORE SENSORS WITHIN MICROFLUIDIC CHANNEL ARRAYS USING CONTROLLED BREAKDOWN

CROSS-REFERENCE TO RELATED APPLICATIONS

This application is a continuation of U.S. patent application Ser. No. 15/537,673, filed on Jun. 19, 2017 which is a U.S. National Phase Application under 35 U.S.C. 371 of International Application No. PCT/162015/059799 filed on Dec. 18, 2015, and published in English as WO 2016/098080 A1 on Jun. 23, 2016. This application claims the benefit of U.S. Provisional Application No. 62/094,669 filed on Dec. 19, 2014. The entire disclosures of the above applications are incorporated herein by reference.

FIELD

The present disclosure relates to fabrication of nanopore sensors inside microfluidic channels by controlled breakdown (CBD) in solid-state membranes.

BACKGROUND

Nanopores are now a well-established class of label-free sensors capable of detecting single molecules electrically. The technique relies on the application of a voltage across a nano-scale aperture in a thin, insulating membrane immersed in an ionic solution. Modulation of the resulting ionic current can be associated with the translocation of individual charged biomolecules such as DNA and proteins that are electrophoretically driven through the nanopore. These changes in conductance provide information about the length, size, charge and shape of translocating molecules. A variety of single-molecule studies, including DNA sequencing, protein detection and unfolding, single-molecule mass spectrometry and force spectroscopy make this technology particularly attractive.

Nanopores may be formed by incorporating proteinaceous pores in lipid bilayer membranes or fabricated in thin, solid-state membranes. The biological pores offer very low noise properties, but the high fragility of the conventionally used lipid bilayer membrane as a supporting structure limits their lifetime and the voltages that can be applied, thus restricting some applications. On the other hand, solid-state nanopores present increased durability over a wider range of experimental conditions, such as applied voltages, temperature and pH, and their size is tuneable in situ. In principle, solid-state nanopores offer a greater propensity to be integrated into robust lab-on-a-chip devices as arrays. In fact, recent studies revealed various integration strategies, which embed such nanopores within microfluidic networks. The nanopores used in these investigations are typically constructed in an ultrathin (10-nm to 50-nm) dielectric membrane (e.g. SiN) using high-energy ion or electron beams. However, the use of FIB or TEM to fabricate nanopores introduces integration challenges. The need for direct line-of-sight access when drilling with beams of energetic particles demands that nanopores be fabricated before their integration within microfluidic devices. This imposes strict alignment requirements during both nanopore fabrication and device assembly, resulting in challenges that limit the yield of functional devices, particularly for array formation on a single membrane or when the dimensions of the microfluidic channels are reduced in order to minimize electrical noise. More generally, these conventional nanofabrication techniques rely on the production of nanopores in a vacuum environment, which inevitably introduces handling risks and wetting issues when transitioning into aqueous solutions for biosensing experiments.

An alternative method of fabricating solid-state nanopores reliably using high electric fields was recently proposed and is referred to herein as nanopore fabrication by controlled breakdown (CBD). In situ and under typical experimental biological sensing conditions (e.g. in 1 M KCl), a dielectric breakdown event is induced in the supporting intact insulating membrane resulting in the formation of a single nanopore with a diameter as small as 1-nm in size but tuneable to large sizes with sub-nm precision. The simplicity of the CBD method lends itself well to the integration of nanopore sensors within complex microfluidic architectures and to potential lab-on-a-chip devices. Combining the advanced sample handling and processing capabilities inherent in microfluidic devices with in situ nanopore fabrication is expected to mitigate various integration issues and expand the range of applications of the sensing platform. Further details regarding this fabrication technique can be found in U.S. Patent Publication No. 2015/0108808 which is entitled "Fabrication of Nanopores using High Electric Fields" and is incorporated by reference herein in its entirety.

This section provides background information related to the present disclosure, which is not necessarily prior art.

SUMMARY

This section provides a general summary of the disclosure, and is not a comprehensive disclosure of its full scope or all of its features.

An apparatus is presented for fabricating one or more nanopores in a membrane. The apparatus includes: a first substrate having a common microchannel formed in an exposed surface of the first substrate; a support structure disposed onto the exposed surface of the first substrate and configured to host a membrane; a second substrate having one or more microfluidic channels formed in an inner surface of the second substrate, the second substrate being disposed onto the support structure with the inner surface facing the support structure such that the one or more microfluidic channels are fluidly separated by the membrane from the common microchannel; and a set of electrodes that generate an electric potential across the membrane. The set of electrodes may include a reference electrode positioned on one side of the membrane and two or more additional electrodes positioned on an opposing side of the membrane, wherein the two or more additional electrodes are arranged in relation to the membrane such that the electric field across the membrane is uniform. In some embodiments, the magnitude of the electric potential across the membrane results in the electric field having a value greater than 0.1 volt per nanometer.

The apparatus further includes: a current sensor electrically coupled to one of the electrodes and operable to measure current flowing between one of the one or more microfluidic channels and the common microchannel; and a controller interfaced with the current sensor, wherein the controller detects an abrupt increase in the measured current which indicates formation of a pore and, in response to detecting the abrupt increase in the measured current, removes the electric potential applied across the membrane.

In one embodiment, the two or more additional electrodes include a first electrode disposed in the one or more microfluidic channels upstream from the membrane and a second electrode disposed in the one or more microfluidic channels downstream from the membrane.

In some embodiments, a plurality of microfluidic channels are formed in inner surface of the second substrate. Each microchannel has an associated set of electrodes. In this way, an array of nanopores (corresponding to the number of microfluidic channels) can be fabricated in the membrane.

In other embodiments, the membrane may be disposed directly onto the first substrate without the use of a support structure. In such embodiments, the set of electrodes may include two reference electrodes disposed in the common microchannel, such that one of the reference electrodes is upstream from the membrane and the other reference electrode is downstream from the membrane.

In another aspect of this disclosure, an intermediate layer is disposed directly onto the support structure and thus in between the support structure and the second substrate. In this case, the apparatus for fabricating one or more nanopores in a membrane includes: a first substrate having a common microchannel formed in an exposed surface of the first substrate; a support structure disposed onto the exposed surface of the first substrate and configured to host a membrane; an intermediate layer disposed onto the support structure and having at least one via formed therein; a second substrate having one or more microfluidic channels formed in an inner surface of the second substrate, the second substrate being disposed on the intermediate layer with the inner surface facing the support structure such that the one or more microfluidic channels are fluidly separated by the membrane from the common microchannel; and a pair of electrodes arranged on opposing sides of the membrane. The pair of electrodes generates an electric potential across the membrane. The one or more vias in the intermediate layer fluidly couples the one or more microfluidic channels with an exposed surface of the membrane and is configured to create an electric field that is uniform in and around the via. In some embodiments, the magnitude of the electric potential across the membrane results in the electric field having a value greater than 0.1 volt per nanometer.

The apparatus further includes: a current sensor electrically coupled to one of the electrodes and operable to measure current flowing between one of the one or more microfluidic channels and the common microchannel; and a controller interfaced with the current sensor, wherein the controller detects an abrupt increase in the measured current which indicates formation of a pore and, in response to detecting the abrupt increase in the measured current, removes the electric potential applied across the membrane.

In some embodiments, a plurality of microfluidic channels are formed in the inner surface of the second substrate. Each microchannel has an associated set of electrodes. In this way, an array of nanopores (corresponding to the number of microfluidic channels) can be fabricated in the membrane.

In other embodiments, the membrane may be disposed directly onto the first substrate without the use of a support structure. In such embodiments, the set of electrodes may include two reference electrodes disposed in the common microchannel, such that one of the reference electrodes is upstream from the membrane and the other reference electrode is downstream from the membrane.

In yet another aspect of this disclosure, the one or more microfluidic channels are routed adjacent to the membrane in a manner that creates an electric field that is uniform across the area of the membrane and thereby reduces the number of required electrodes. In one embodiment, the microfluidic channel forms a loop downstream from the electrode disposed in the channel, where a section of the loop is routed over the membrane.

In some embodiments, one or more control valves are disposed in the microfluidics channel and operate to control amount of flow through the microfluidic channel. The control valve may be implemented by an elastomeric polymer fluidly coupled to and actuated by a pneumatic source.

In some embodiments, a plurality of microfluidic channels are formed in the inner surface of the second substrate. Each microchannel has an associated set of electrodes. In this way, an array of nanopores (corresponding to the number of microfluidic channels) can be fabricated in the membrane. In addition, each microfluidic channel in the array of microfluidic channels passes over a portion of the membrane and has at least two control valves disposed therein, one valve is disposed upstream of the membrane and the other value disposed downstream of the membrane. In this way, the value of the electric potential across the membrane is controlled by adjusting flow through the control valves disposed in the array of microfluidic channels.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 4A-4C are schematics depicting different electrode arrangements, which may be used to create a uniform electric field across the surface area of the membrane.

curves used to infer nanopore diameter using a conductance-based model for five independently fabricated nanopores on a single five-channel device.

Figure 8A:
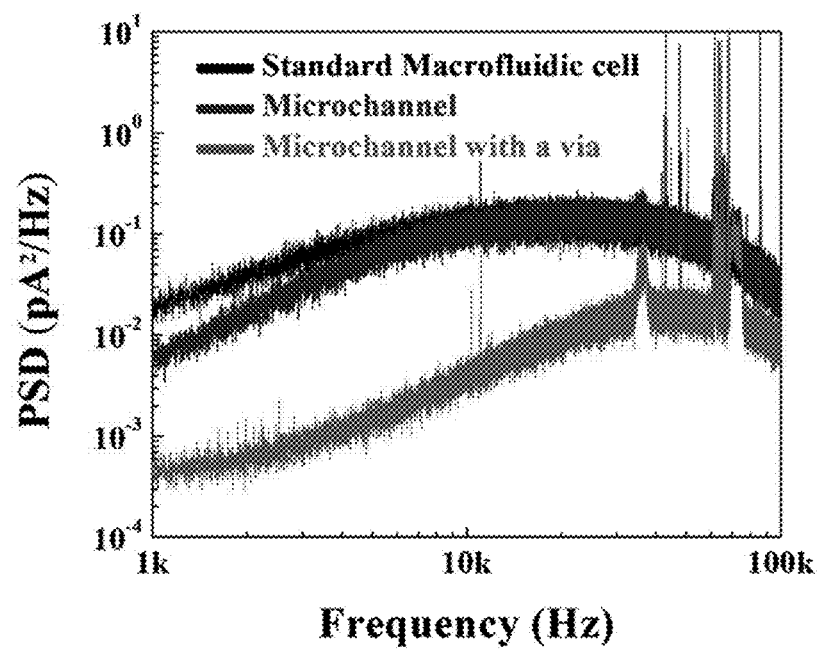
Figure 8B:
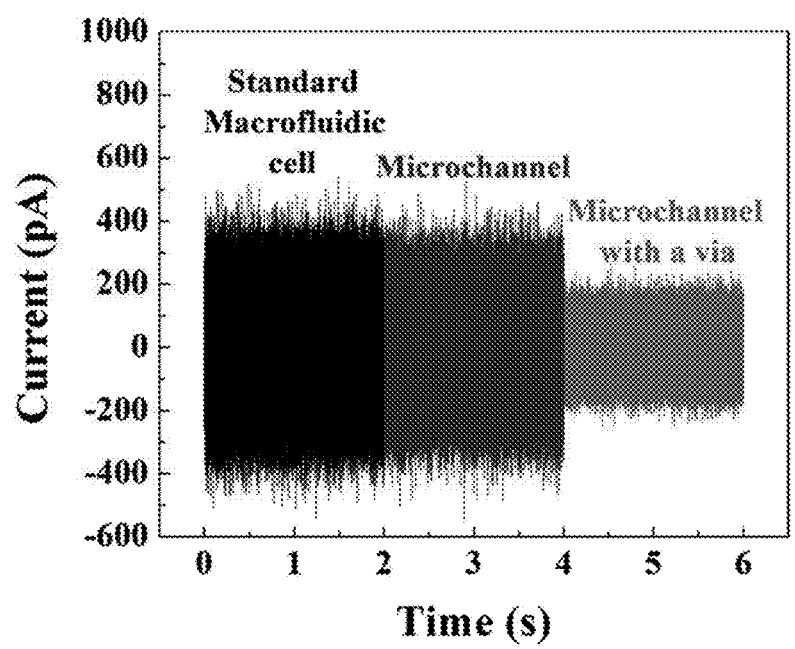

FIGS. 8A and 8B are graphs showing (a) power spectral density (PSD) noise comparison; and (b) current traces, respectively, in a macroscopic cell (black), five-channel device (blue) and five-channel device with micro-vias (red). All measurements were done in the absence of any fabricated nanopore at no applied voltage, sampled at 250 kHz and low-pass filtered at 100 kHz by a 4-pole Bessel filter in 1 M KCl pH 7.5.

Figure 9A:
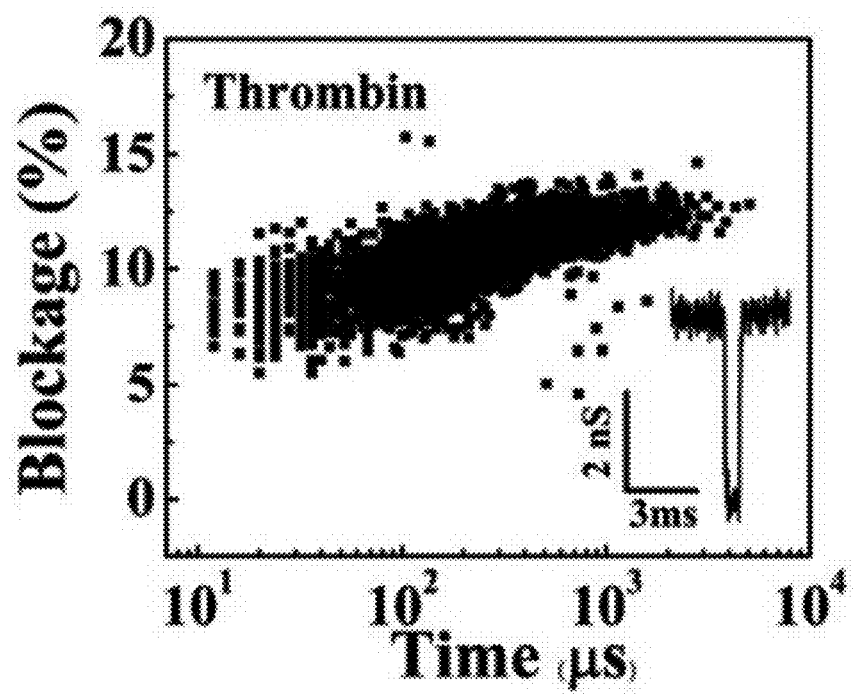
Figure 9B:
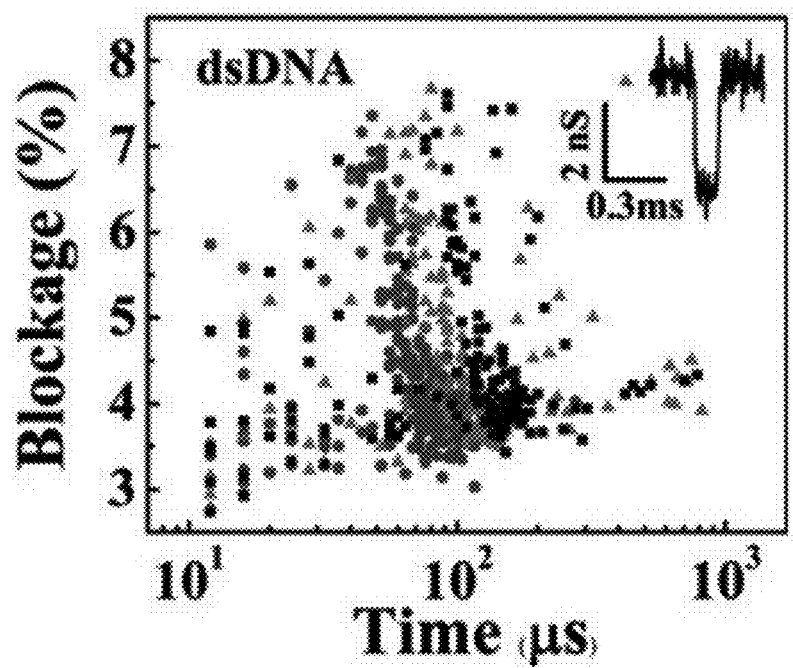

FIGS. 9A and 9B are scatter plots of the normalized average current blockade (0% representing a fully opened pore, and 100% a fully blocked pore) versus the total event duration of (a) human α-thrombin detection using a 10.5-nm pore for −200 mV applied voltage, and (b) 10-kb dsDNA translocation through a 11.5-nm pore at −200 mV (black squares), −250 mV (red triangles) and −300 mV (blue circles), respectively. Each data point represents a single event. The insets show transient current blockades as biomolecules interact with the nanopore. For clarity the data was multiplied by −1 in the insets.

Figure 10A:
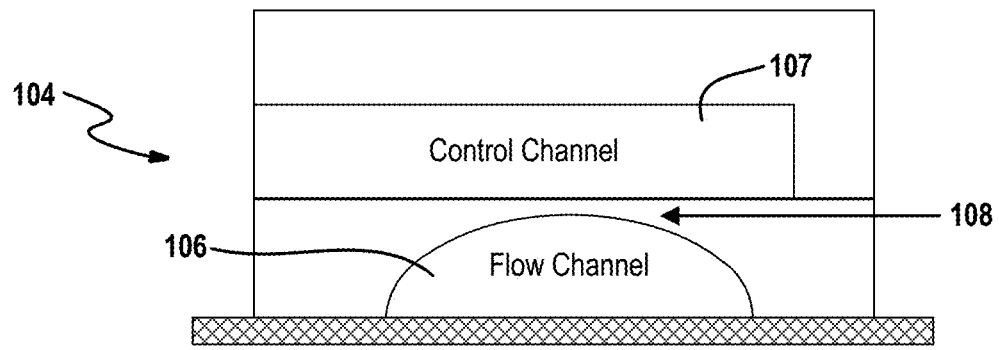
Figure 10B:
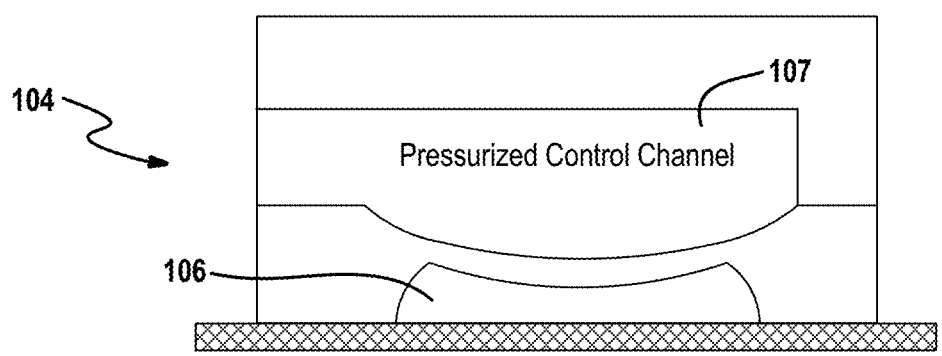

FIGS. 10A and 10B are cross section view of an example micromechanical pneumatic valve without and with pressure applied to the control channel, respectively.

Figure 11:
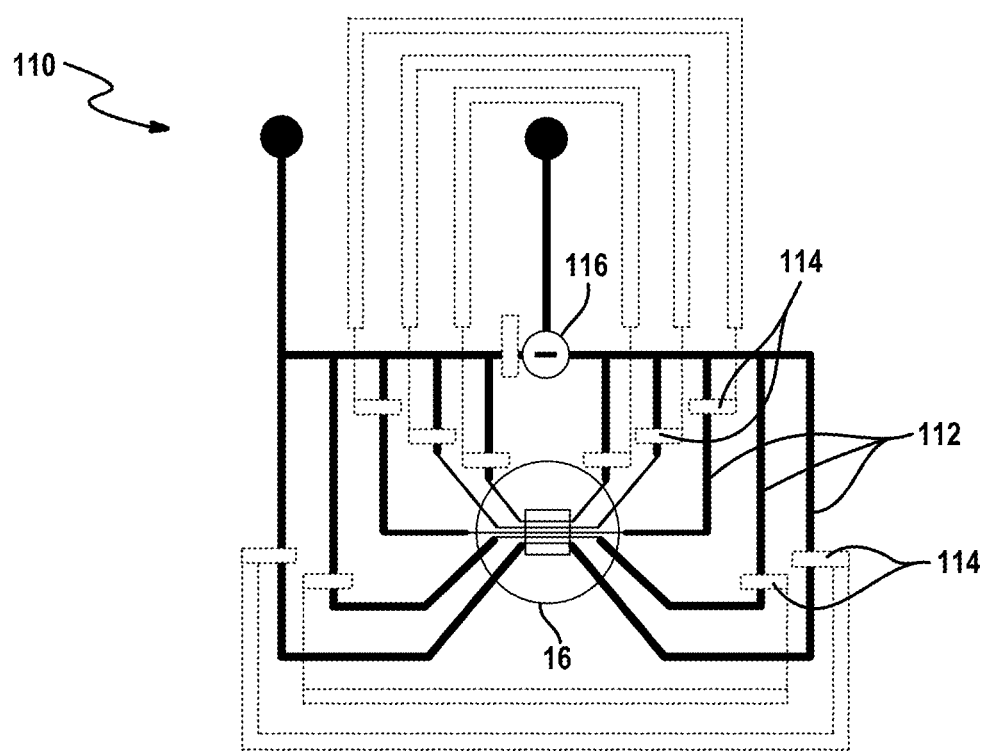

FIG. 11 is a schematic top view of a 5×1 array device with five pairs of pneumatic valves and employing a single pair of electrodes.

Figure 12:
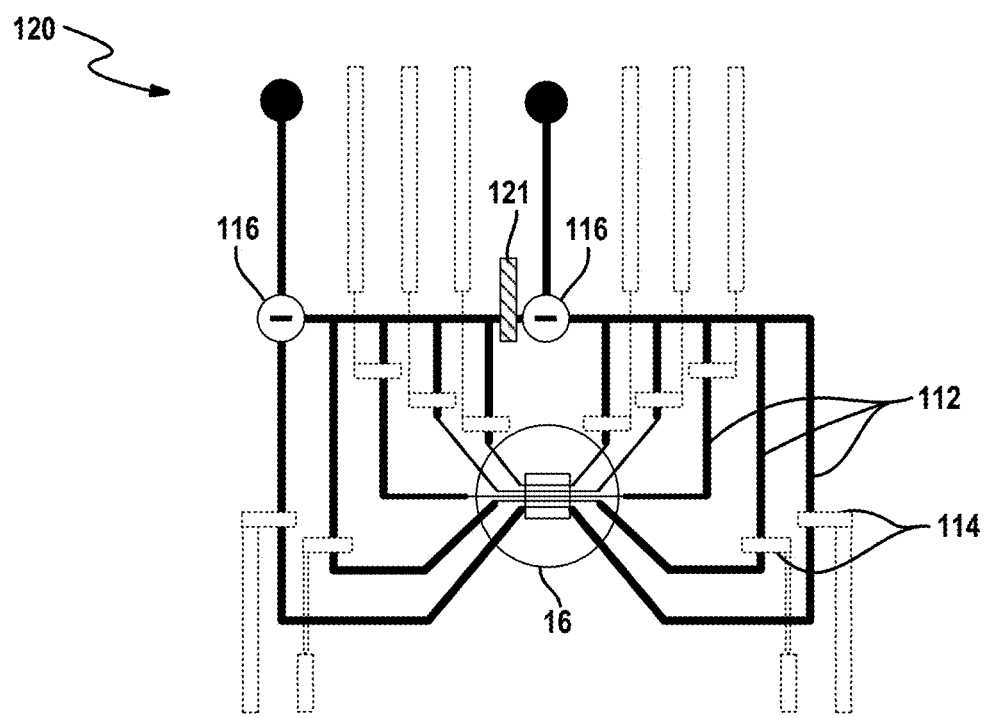

FIG. 12 is a schematic top view of a 5×1 array device which employs two top electrodes.

Figure 13:
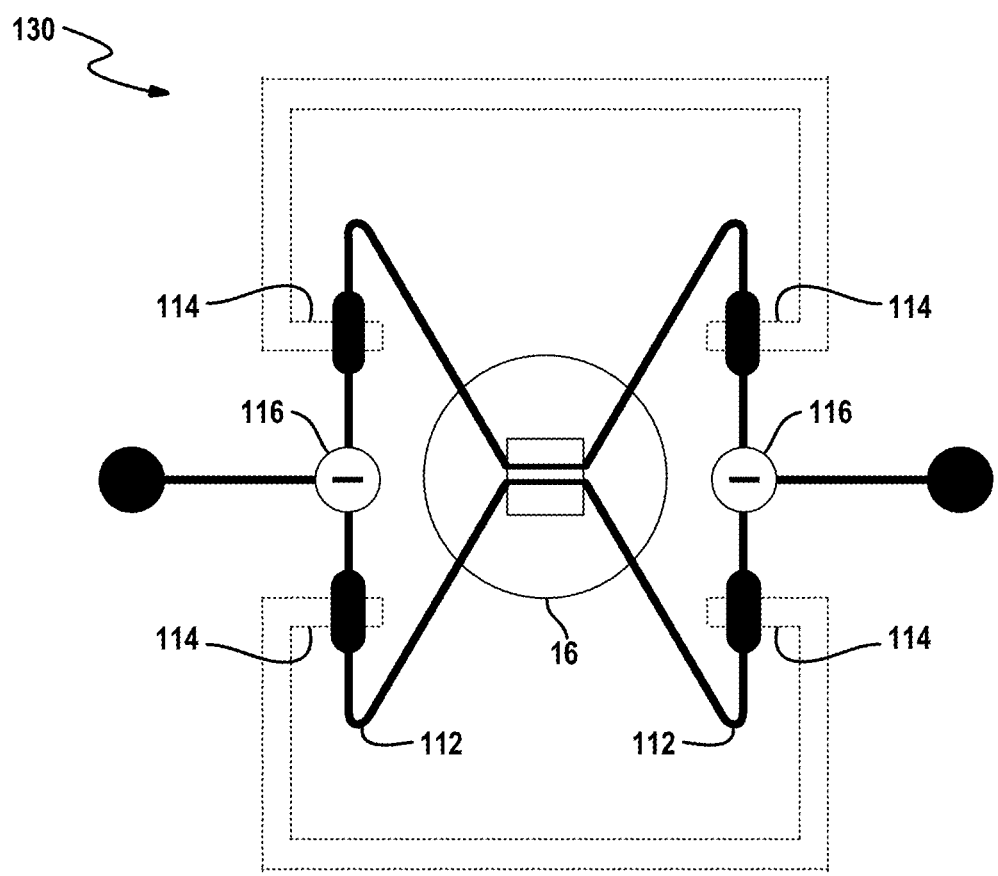

FIG. 13 is a schematic top view of a 2×1 array device with two pairs of pneumatic valves and two top electrodes.

Corresponding reference numerals indicate corresponding parts throughout the several views of the drawings.

DETAILED DESCRIPTION

Example embodiments will now be described more fully with reference to the accompanying drawings.

Figure 1:
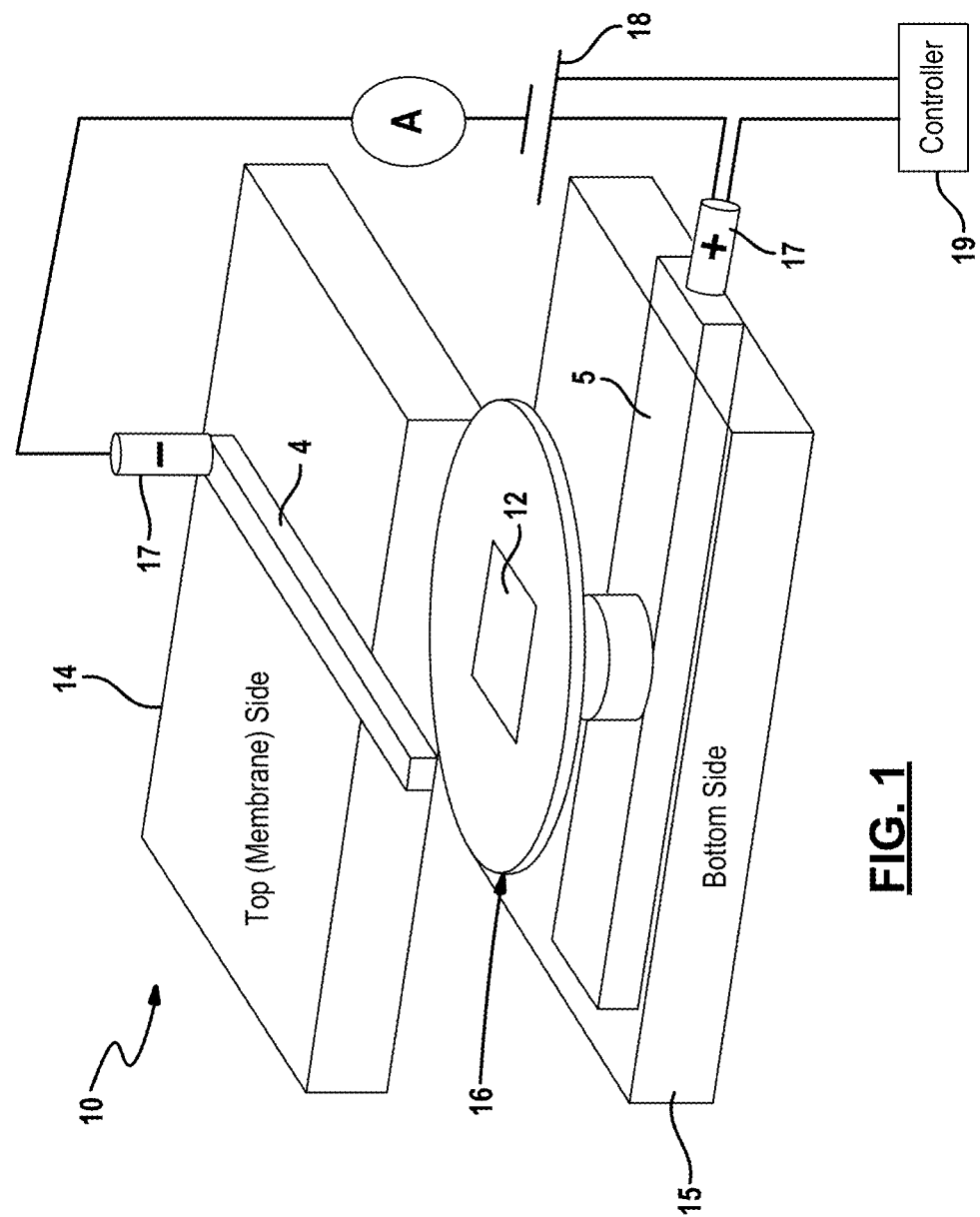
FIG. 1 is a schematic of an apparatus for fabricating nanopores with a single electrode inserted on either side of the membrane.

FIG. 1 depicts an apparatus 10 for fabricating one or more nanopores in a membrane 12. The apparatus is comprised generally of a top (first) substrate 14, a bottom (second) substrate 15, and a support structure 16 disposed between the top and bottom substrates 14, 15. The support structure 16 is configured to host a thin dielectric membrane 12 that defines opposing planar surfaces 13. For illustration purposes, a single microfluidic channel 4 is formed in the top substrate 14 and a larger common microfluidic channel 5 is formed in the bottom substrate 15. A pair of electrodes 17 electrically coupled to a voltage source 18 are used to generate an electric potential across the membrane; with a single electrode placed in each microfluidic channel 4, 5. As will be further described below, the apparatus may have more microfluidic channels with differing electrode arrangements.

The apparatus 10 further includes a current sensor (not shown) electrically coupled to one of the electrodes and a controller 19 interfaced with the current sensor and the voltage source 18. During operation, the current sensor measures currents flowing across the membrane. The controller 19 in turn detects an abrupt increase in the measured current and, in response to detecting the abrupt increase in the measured current, removes the electric potential applied across the membrane as will be further described below.

Figure 2B:
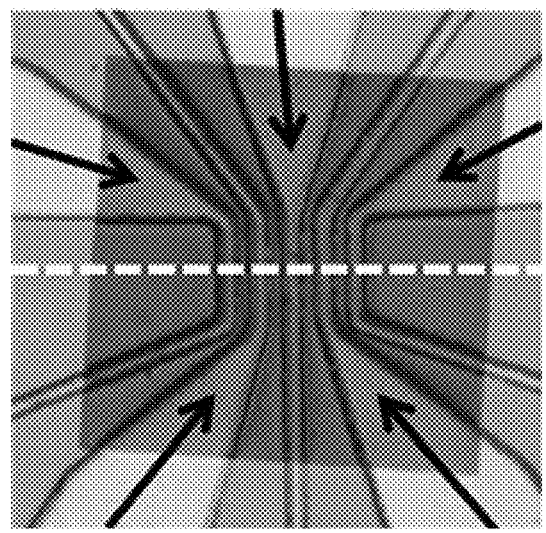
FIGS. 2A and 2B are a cross-section view of an example embodiment of the apparatus having five independent microfluidic channels; and reflected optical images taken from above the apparatus with the five microfluidic channels situated directly on the membrane, respectively.
Figure 2A:
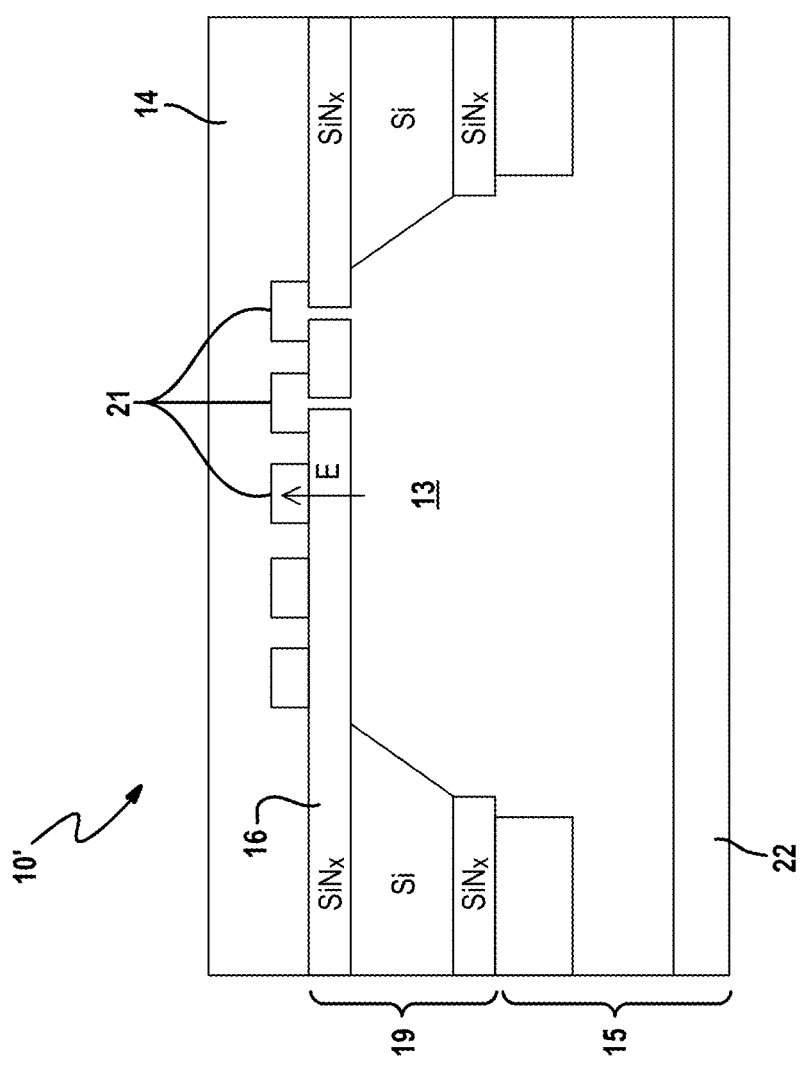

FIGS. 2A and 2B further depict an example embodiment of the apparatus 10'. In this example embodiment, commercially available silicon chips (e.g., 3-mm frame size) possessing an exposed 500×500-µm2, 20-nm thick SiN membrane (SiMPore Inc. SN100-A20Q05) serves as the support structure 16 and were mounted between microfluidic channel arrays of differing architectures. Referring to FIG. 2A, the apparatus 10' presented herein utilized geometries containing five independently addressable microfluidic channels 21 on one side of the membrane 12, while the other side of the membrane 12 was accessed by a single common microchannel 22. More specifically, the apparatus 10' included an array of five independent microfluidic channels 21 consisting of broad 200-µm wide channels (50-µm height) tapering over the membrane 12 to a 15-µm width as best seen in FIG. 2B. Each of the five independent channels 21 is separated from one another by 25-µm. While five independent microfluidic channels are shown in this embodiment, it is readily understood that more or less microfluidic channels can be formed in other embodiments.

In the example embodiment, each layer was fabricated by soft lithography using polydimethylsiloxane PDMS (Sylgard 184 from Dow Corning at a 7:1 (w/w) ratio), patterned from a master mould prepared by soft photolithography. In all configurations, the bottom layer consisted of a ~3-mm thick layer of PDMS containing a single 250-µm wide by 100-µm high fluidic channel 22 bonded to a glass slide (oxygen plasma bonding, AutoGlow Research). In order to allow fluidic access to the nanopores, a 2-mm hole was hand-punched through this common bottom microchannel 22 over which the etched side of the silicon chip was seated. A thin layer (100±10-µm) of PDMS was then spin-coated around the chip 16 to compensate for the thickness of the silicon chip and to leave a smooth, sealed surface upon which the multiple microfluidic channels could be bonded. After spin coating, this thin PDMS layer was cured on a hot plate at 80° C. for 20 minutes.

Figure 3A:
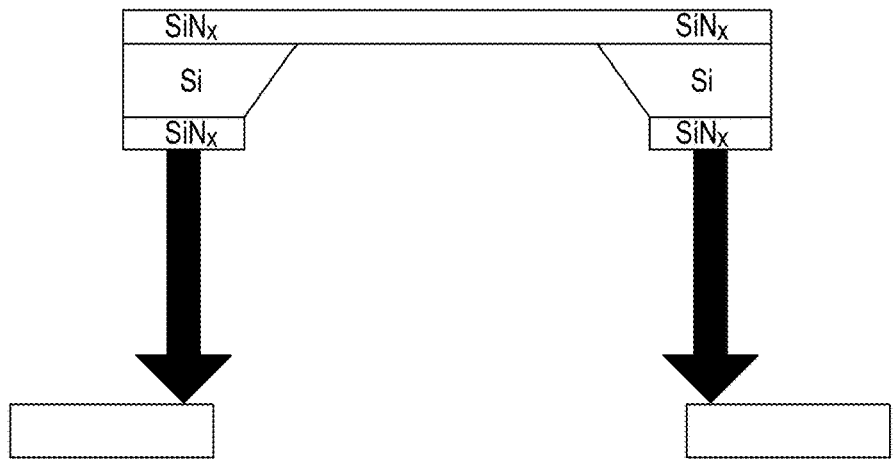
FIGS. 3A-3C are schematics depicting an example assembly method for the apparatus shown in FIG. 2A.
Figure 3B:
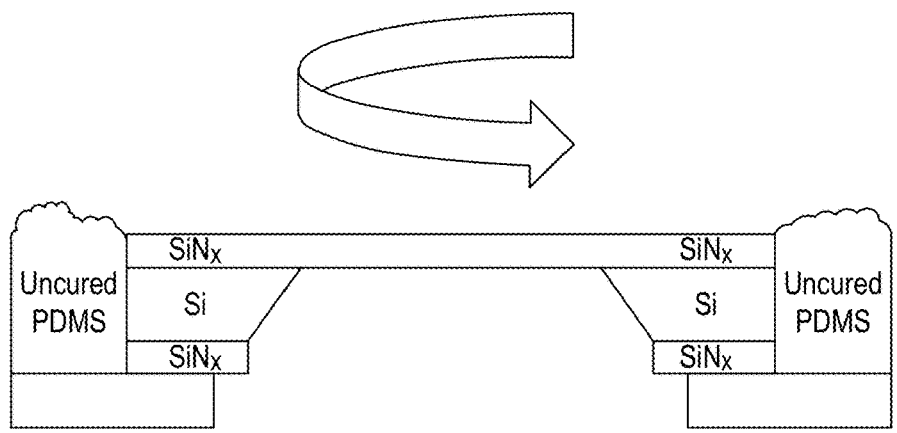
Figure 3C:
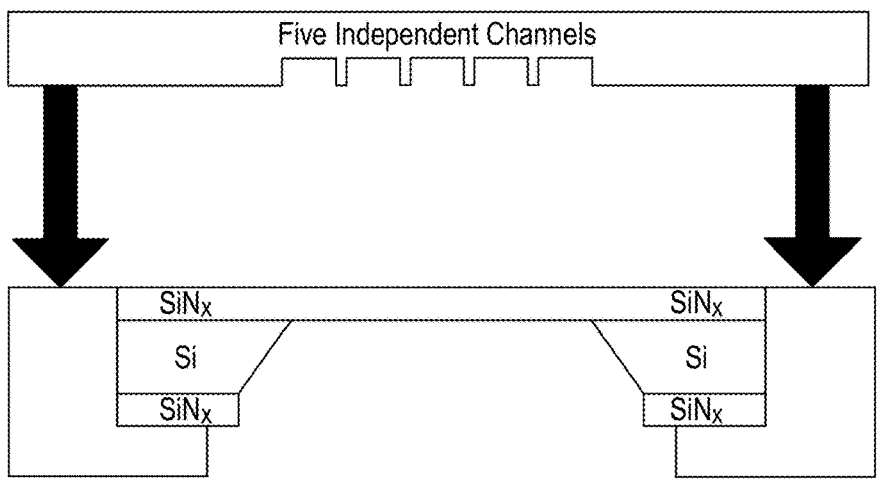

FIGS. 3A-3C further illustrates this fabrication process. The devices presented integrate commercially available silicon nitride (SiN) membranes (SN100-A20Q05, SiMPore Inc.) within microfluidic devices made of polydimethylsiloxane (PDMS). PDMS layers were replicated from a master mould fabricated by soft lithography and made of SU8-2050 photoresist (Microchem Inc.) on a silicon wafer. Each microfluidic layer (microfluidic via, independent and common channel layers) were fabricated using different spin speeds, baking time and temperature, UV exposure and developing times depending on the final desired thickness (height) of the resultant features Following the fabrication of each master mould, wafers were first treated with aminosilane to facilitate PDMS removal. PDMS (7:1 (w/w) base:curing agent for all layers) was then poured over the master mould for each channel layer, followed by degassing in a vacuum chamber for 30 minutes and baking at 80° C. for 2 hours. The cured PDMS was then peeled off the mould to create the microchannel structure. Individual device components were then cut out and access holes for fluid and electrode introduction were punched through the independent channels (0.75 mm OD for fluidic tubing and 1.25 mm OD for electrodes). A 2.0 mm hole also was hand-punched in the middle of the common microchannel to allow fluidic access to the bottom of the chip. With reference to FIG. 3A, the silicon chip (etched side) was then bonded to the common channel layer atop the punched hole using oxygen plasma (Glow Research AutoGlow). All plasma bonding steps were performed at 30 W for 30 seconds.

In order to compensate for the thickness of the silicon chip and leave a leveled, smooth surface for bonding of the independent (top) channels in both configurations (with and without microfluidic via layers), a thin layer (~100±10 μm) of PDMS was spun around the chip (5 @ 500 rpm followed by 10 s @ 1000 rpm). This thin layer was cured directly on a hot plate at 80° C. for 20 minutes.

In order to allow fluidic and electrical access to the microfluidic channels, holes were punched through each of the top fluidically separated and bottom common channels prior to bonding to accommodate tight fitting of Ag/AgCl electrodes and PEEK tubing flowing electrolyte (or ionic) solution. By placing the electrodes ~5-mm from the centre of the membrane, the resistance of the microchannel leading up to the nanopore is limited to ~100 kΩ in 1M KCl electrolyte solution, less than ~1% of the total electrical resistance of a device containing a nanopore with a diameter of 10-nm. Finally, the common channel was bonded to a clean glass slide. While reference has been made to a particular fabrication technique, it is understood that other lithographic techniques also fall with the scope of this disclosure.

Immediately prior to introducing electrolyte solution into the microfluidic channels, the assembled device was treated with oxygen plasma for 5 minutes at 70 W to increase microchannel hydrophilicity. The microfluidic channels were then connected to sample vials with polyethylene tubing and flow was initiated by pressurizing the vials using high-precision pressure regulators. Effective sealing (>10 GΩ) between microfluidic channels was tested prior to nanopore fabrication by flowing 1 M KCl solution (pH 7.5) and attempting to measure the ionic current between microfluidic channels under a moderate applied voltage (e.g., 0.2V-1V).

In order to improve the functionality of the apparatus, contaminants and monomers should be removed from the microfluidic material used to make the apparatus. In particular, polydimethylsiloxane (PDMS) pieces should be chemically treated with solvents prior to assembling the device and plasma treatments can be used to remove contaminants on the membrane surface as a result of microfluidic integration.

In accordance with one aspect of this disclosure, electrode placement within microfluidic channels should result in a uniform electric field over the area of the insulating membrane. Various electrode placements can be used depending on the microfluidic architecture as seen in FIGS. 4A-4D. In the case of a single microchannel laid over the thin insulating membrane, a single pair of electrodes positioned on either side of the membrane, somewhere down the length of microfluidic channels, will produce a non-uniform electric field across the membrane surface. However, placing two electrodes biased at the same electric potential, in the same microfluidic channel but on both sides of membrane (i.e., one electrode upstream from the membrane while the other electrode is downstream from the membrane), can increase the electric field uniformity as best seen in FIG. 4A. In this example, a set of electrodes 30 are used to generate an electric potential across the membrane 12. The set of electrodes 30 includes a reference electrode 33 positioned below the membrane and two or more additional electrodes 32 positioned above the membrane. More specifically, the two electrodes 32 are positioned in the microfluidic channel of the top substrate; whereas, the reference electrode 33 is positioned in the common microfluidic channel of the bottom substrate. The two additional electrodes 32 are arranged in relation to the membrane such that the electric field across the membrane is uniform. For example, one of the additional electrodes 32 may be disposed upstream from the membrane while the other of the additional electrodes 32 may be disposed downstream from the membrane. Other placements for the two additional electrodes are also contemplated by this disclosure.

With reference to FIG. 2A, the underside of the support structure 16 includes a tapered recess 13 which helps shape the electric field in a uniform manner, similarly to the role played by the via, and thereby enables the use of a single reference electrode 33.

In some embodiments, the membrane 12 may be placed directly onto and supported by the bottom substrate 15 without the use of a support structure 16. In these embodiments, a second reference electrode 33 can be placed on the underside of the membrane as seen in FIG. 4C. In particular, one of the reference electrodes 33 is disposed upstream from the membrane while the other of the two reference electrodes 33 may be disposed downstream from the membrane. In this way, the two reference electrodes 33 functions to shape the electrode field proximate to the membrane in a uniform manner.

FIG. 4B depicts an alternative electrode arrangement. In this arrangement, a single electrode 35 is position within a looped microfluidic channel 36 containing ionic solution to achieve a similarly uniform electric field across the membrane surface. The microfluidic channel 36 forms a loop downstream from the electrode 35 and a section of the loop is routed over the membrane. The valve in such an apparatus is pressurized, closing the underneath flow channel. During the nanopore fabrication process, the pressure of the valve will be released (microfluidic channel is opened). In this way, the presence of the electrolyte solution through the looped channel will shape the electric field in a uniform manner. This configuration is scalable to several microfluidic channels using microvalve technology (e.g., as seen in FIG. 11). In this alternative arrangement, it is understood the single reference electrode 33 may be positioned under the membrane as described in relation to FIG. 4A or two reference electrodes may be used as described in relation to FIG. 4B.

Microelectrodes can also be patterned within the microfluidic channels to achieve similarly uniform electric fields. These surface patterned electrodes, held at the same potential, can be positioned as described above to result in a uniform electric field. Circular electrodes centered about the insulating membrane can also ensure field uniformity. A single patterned microelectrode can be patterned directly above the insulating membrane or inside of each individual microfluidic channel. Such surface-patterned electrodes would be particularly beneficial on custom-designed chips where large-scale arrays of nanopore can be formed. Other variants for electrode arrangements that result in a uniform electric field are also contemplated by this disclosure.

Figures 5A, 5B:
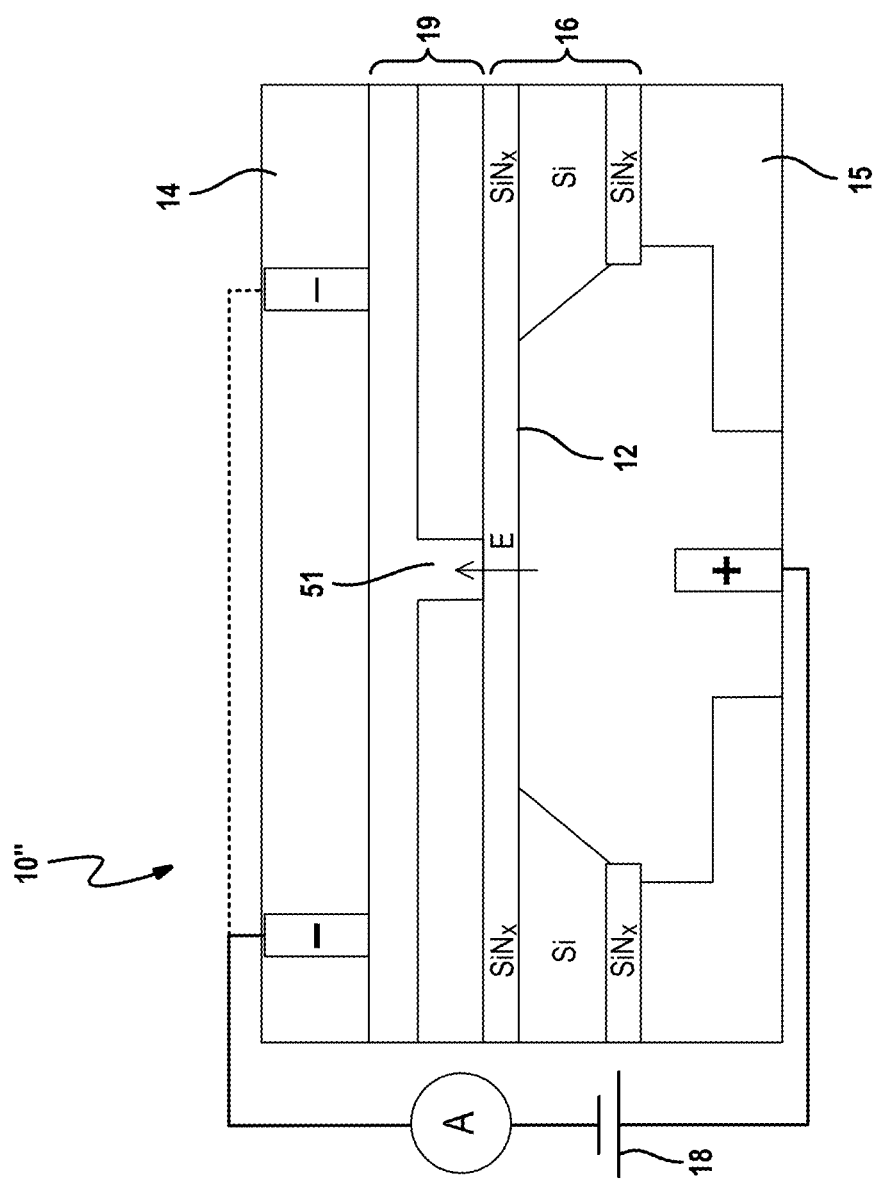
FIGS. 5A and 5B are a cross-section view of a second example embodiment of the apparatus with a micro-via layer; and reflected optical images taken from above the apparatus with five microfluidic channels situated directly on the membrane but isolated from the membrane by a micro-via layer.

In another aspect of this disclosure, micro-vias can be added to the microfluidic system to help shape the electric field in and around the via. FIGS. 5A and 5B depict a second example embodiment of the apparatus 10". In this embodiment, the apparatus is again comprised of a top substrate 14, a bottom substrate 15, and a support structure 16 disposed between the top and bottom substrates. The support structure 16 is likewise configured to host a thin dielectric membrane 12 that defines opposing planar surfaces 13. In this embodiment, an intermediate layer 19 is formed on the support structure 16 and disposed between the top substrate 14 and the support structure 16. One or more vias 51 can be formed in the intermediate layer 19 and configured to create an electric field that is uniform in and around the via.

This second microfluidic configuration was designed to localize nanopore formation by CBD in each microchannel at the center of the membrane, and to further reduce high frequency electrical noise by minimizing the area of the membrane exposed to the ionic solution. In this second configuration, a 200-μm thick layer of PDMS with an array of rectangular apertures, varying in length from 40-μm to 120-μm with a constant width of 15-μm, was used to form microfluidic vias linking the microfluidic channels to a well-defined area over the center of the membrane. To fabricate thin (200 μm) microfluidic via layers upon which independent channels could be bonded, degassed PDMS was spun on its master mould (5 s @ 500 rpm followed by 10 s @ 800 rpm) and cured directly on a hotplate at 80° C. for 30 minutes. In order to precisely situate microfluidic vias and independent channel layers atop the SiN membrane, all alignment steps were done using an OAI DUV/NUV mask aligner (Model 206). This layer was then bonded to the array of five independent PDMS microfluidic channels as in the initial design. Except as noted above, the second embodiment of the apparatus 10'' was fabricated in the same manner as described in relation to FIGS. 3A-3C.

In order to understand the effects of adding a micro-via layer to the microfluidic configuration, finite element modeling of the electric field in both device geometries (with and without a microfluidic via) was explored. Device configurations were generated in 2D and electric fields were modeled using a stationary study within the Electric Currents module of COMSOL Multiphysics Modeling Software. Both geometries were examined first with an intact membrane (no aqueous connection across the membrane) and then with a nanopore (20-nm fluidic conduit through the membrane).

Figure 6A:
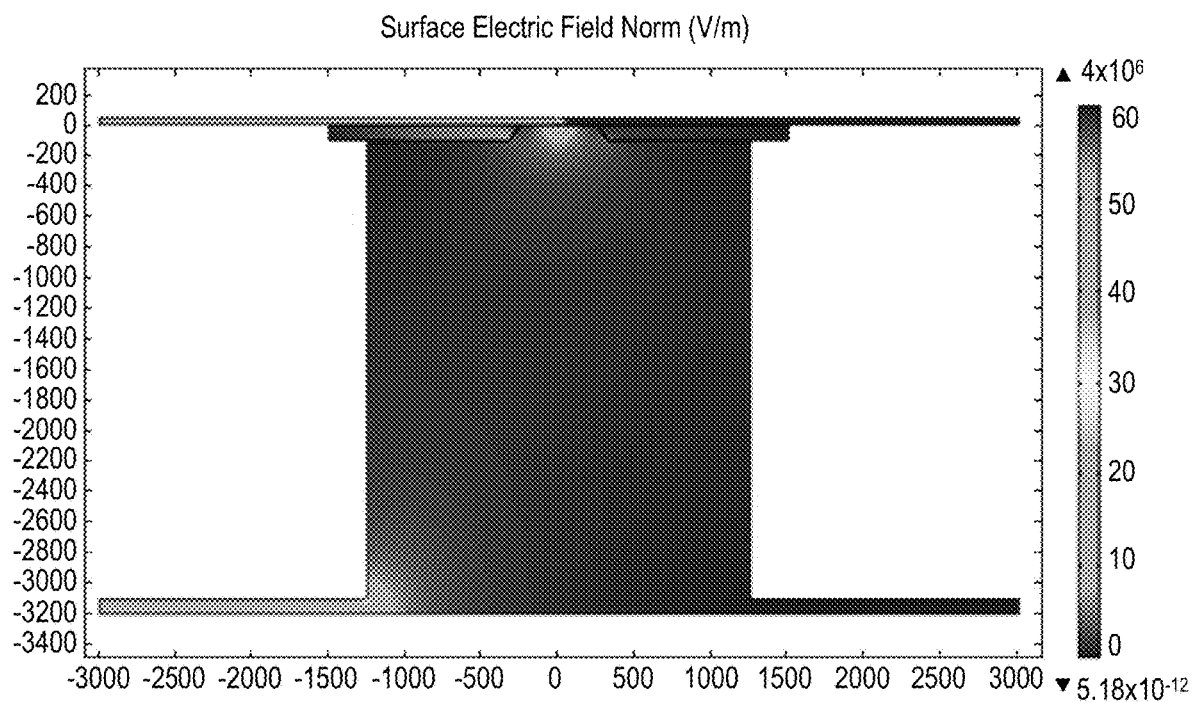
FIGS. 6A and 6B are images showing finite element modelling of the electric field in the apparatus with and without a microfluidic via, respectively.
Figure 6B:
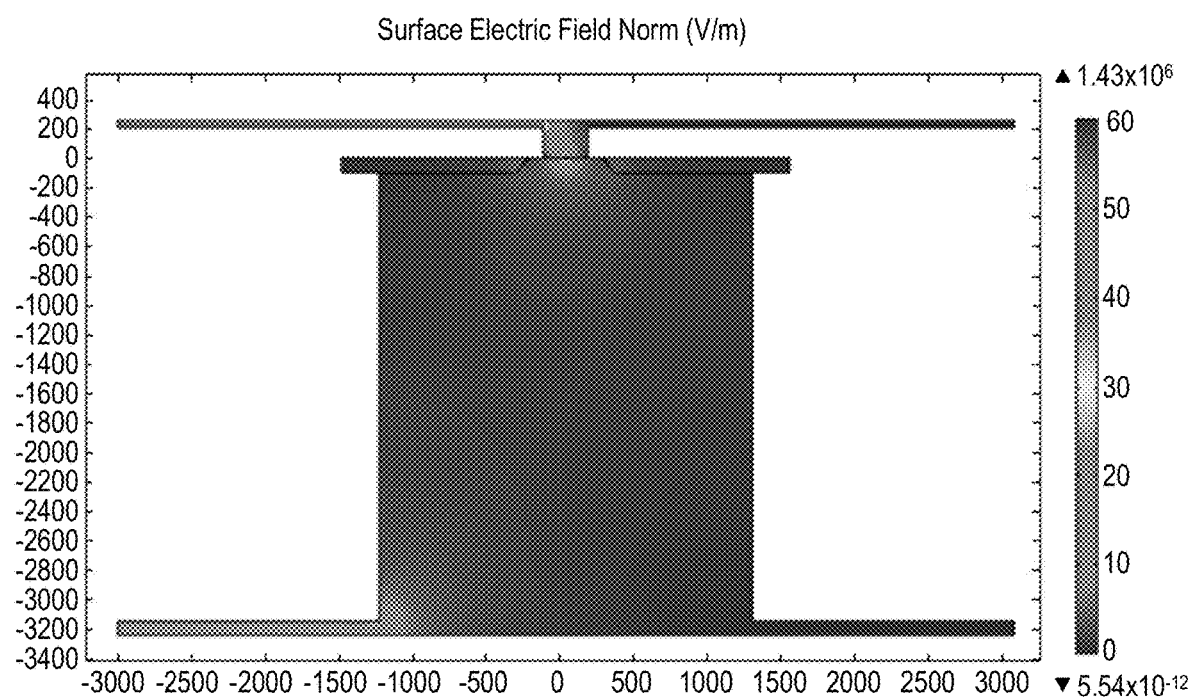
Figure 6C:
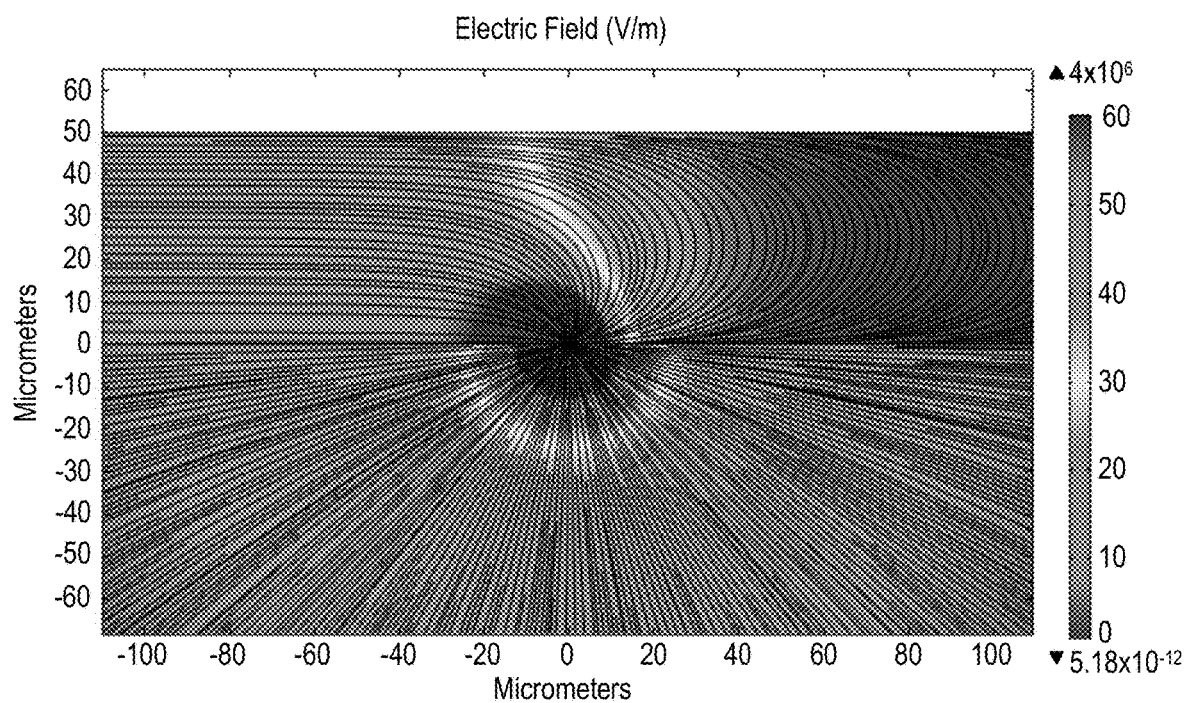
FIGS. 6C and 6D are zoomed in images of the electric field surrounding the nanopore shown in FIGS. 6A and 6B, respectively.
Figure 6D:
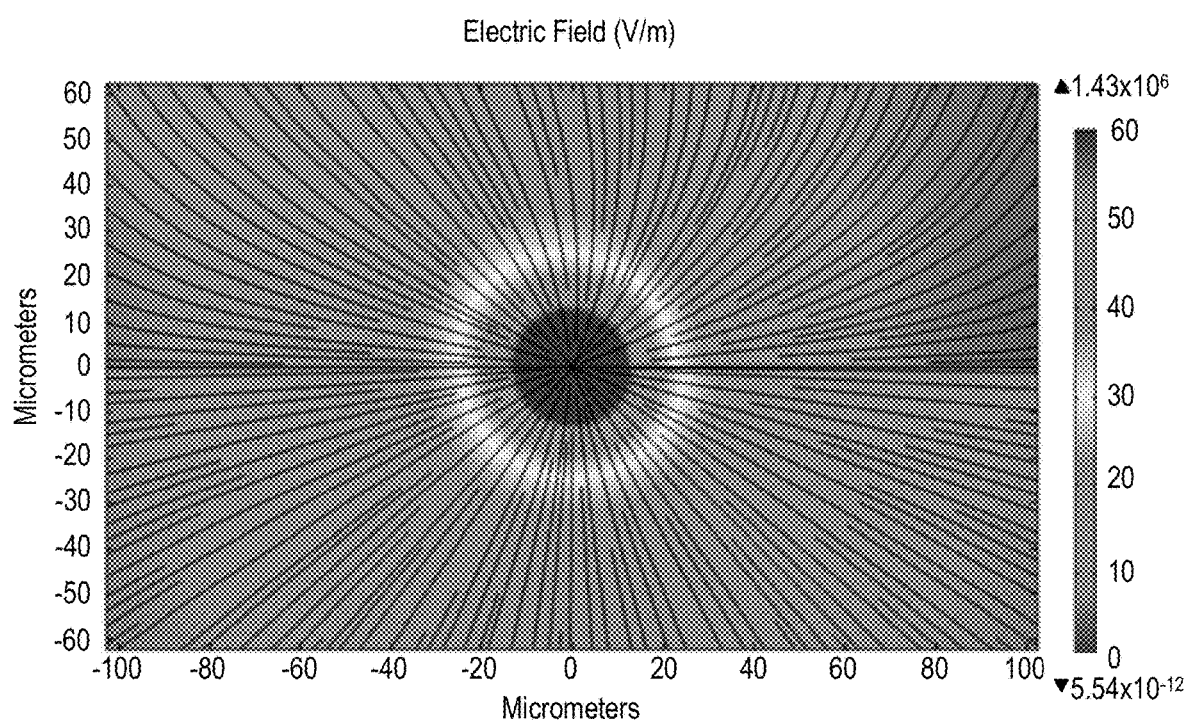

FIGS. 6A and 6B show the geometry of a device with an independent microchannel placed directly on the membrane; and a device containing a microfluidic via, respectively. Both devices contain a 20-nm pore in the centre of the membrane. A zoom of the area surrounding the nanopore in FIG. 6D shows that the electric field in the immediate vicinity of the nanopore in the microfluidic via configuration is relatively uniform across the membrane and the pore. This is highlighted by the fact that the intensity of the electric field decays uniformly away from the nanopore on either side of the membrane. Furthermore, the electric field lines are symmetric from left to right despite the fact that both electrodes are placed 3 mm to the left of the nanopore. Conversely, FIG. 6C shows that the electric field lines are quite non-uniform under the same conditions in a device without a microfluidic via. Both the electric field lines and the field intensity differ both across the membrane and from left to right in the independent (top) microchannel.

Figure 6E:
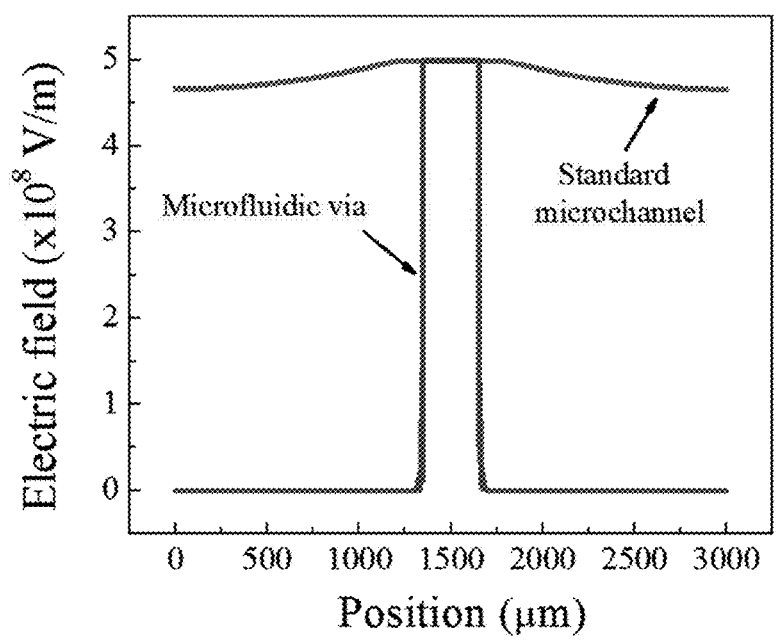
FIG. 6E is a graph depicting the magnitude of the electric field measured along the plane mid-way through the 20-nm thick SiN membrane when a potential difference of 10 V is applied (as in nanopore fabrication).
Figure 6F:
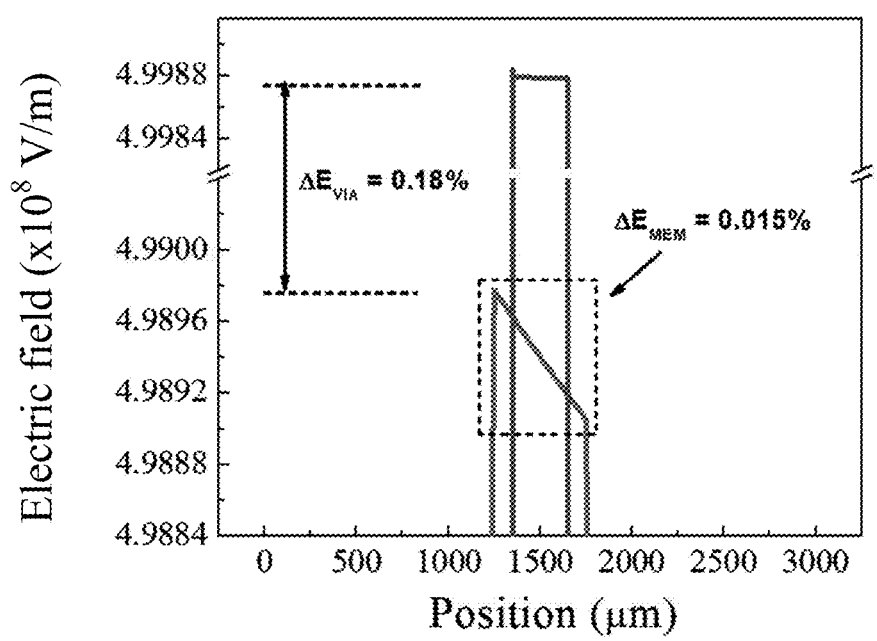
FIG. 6F is a graph depicting the magnitude of the electric field for an apparatus without a microvia.

Further investigation of the electric field shape in these configurations shows that nanopore fabrication using CBD may also be affected by asymmetric placement of electrodes. FIG. 6E shows the magnitude of the electric field though a horizontal cross section of an intact membrane in devices with and without microfluidic vias. In this example, a potential difference of 10 V was applied across the membrane in order to simulate the nanopore fabrication conditions used in practice. While the device containing a microfluidic via exhibits a uniform electric field across the length of the exposed membrane, the device in which the independent (top) microchannel is placed directly on the membrane exhibits a stronger electric field closer to the side where the electrodes are placed.

Figure 7A:
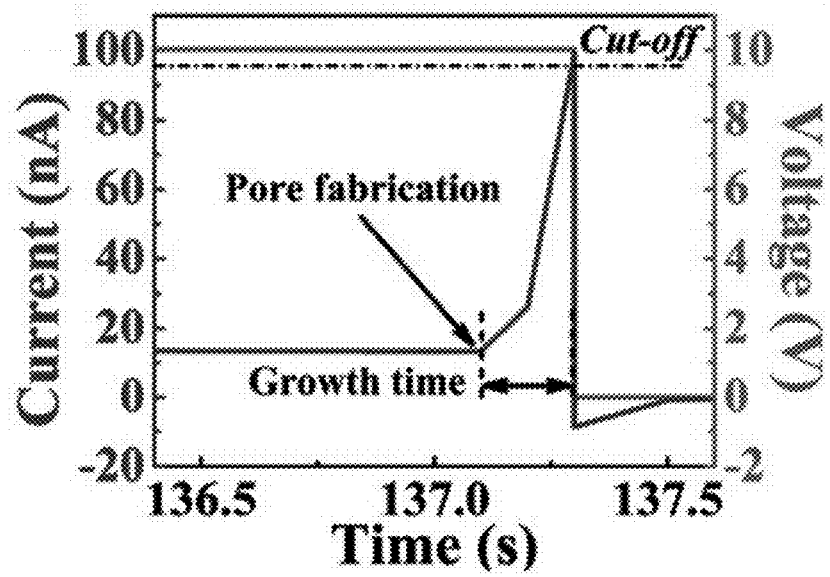
FIGS. 7A and 7B are graphs showing (a) leakage current through the SiN membrane a few seconds before nanopore fabrication by CBD at 10 V; and (b) Current-voltage (I-V)
Figure 7B:
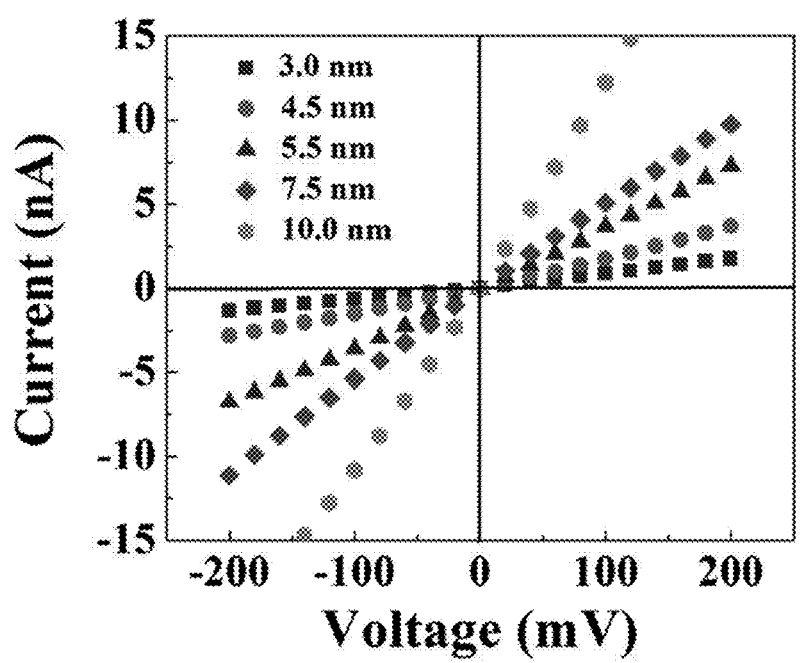

For both example embodiments, individual nanopores were fabricated by inducing a discrete dielectric breakdown event in each of the independent microfluidic channels integrated over the membrane. Briefly, this was done by applying high electric fields using custom-build electronic circuitry. A potential difference ranging from 10 V to 14 V was applied to one of the independent microfluidic channels relative to the grounded common microchannel to fabricate a nanopore in minutes or seconds. The magnitude of the electric potential across the membrane results in the electric field having a value greater than 0.1 volt per nanometer. This potential difference also induced a leakage current through the SiN membrane, which is monitored in real-time (see FIG. 7A). The formation of a single nanopore is detected by the sudden and abrupt increase of the leakage current past a pre-defined threshold, whereby the applied voltage was cut off with a response time of 0.1 s. While the threshold current and response time can be varied to achieve a desired resultant nanopore size following the breakdown event, those discussed here were typically sub-2-nm in diameter (tight cut-off conditions). This process is then repeated in each top fluidically separated microchannel resulting in independently addressable nanopores on a single membrane but located in different microfluidic channels. Following nanopore fabrication, sensitive measurements for electrical characterization and single-molecule sensing were performed using an Axopatch 200B (Molecular Devices) low-noise current amplifier.

In order to obtain nanopores of the desired size for the detection of specific biomolecules, each nanopore was fabricated as described above and then conditioned using high electric fields shaped by the application of alternating −5 V and +5 V pulses across the membrane. This treatment was used to optimize the electrical noise properties and rejuvenate clogged nanopores for further experiments with comparable results to those reported in previous studies which used macroscopic fluidic reservoirs. Further details regarding this conditioning technique can be found in U.S. Patent Publication No. 2015/0109008 which is entitled 'Method for Controlling the Size of Solid-State Nanopores" and is incorporated by reference herein in its entity.

To infer the diameter of each nanopore fabricated by CBD, its conductance G was measured directly in solution by monitoring the ionic current passing through each nanopore as an applied potential difference was swept from −200 mV to +200 mV. By assuming a cylindrical geometry and accounting for access resistance, 30 the effective diameter, d, of the nanopore can be calculated from its conductance by the following relationship:

$$G = \sigma\left(\frac{4L}{\pi d^2} + \frac{1}{d}\right)^{-1} \quad (1)$$

In Eq. 1, σ is the bulk conductivity of the electrolyte and L is the effective length of the nanopore, assumed to be equal to the nominal thickness of the SiN membrane. The current-voltage (I-V) curves in FIG. 2(*c*) displays an ohmic response in 1 M KCl pH 7.5 (σ=10.1±0.1 Sm−1) for five independently formed nanopores ranging in size from 3-nm to 10-nm in a single five-channel device. The error incurred by ignoring the contribution from surface charge in equation 1 affects the accuracy of the effective calculated nanopore diameter by <0.5-nm for the high salt concentrations used here, while the error attributed to the values of the electrolyte conductivity and the membrane thickness affects the uncertainty of the nanopore diameter by ~0.3-nm.

To further characterize performance, power spectral density plots (PSDs) of the ionic current were acquired for nanopores fabricated in each of the two microfluidic architectures (see FIG. 8A). While low-frequency noise (below 1 kHz) is typically of the 1/f-type, higher frequency noise is governed by the dielectric properties and capacitance of the device arising from the surface area exposed to the electrolyte solution. Thus, minimizing the surface exposed to the solution leads to a reduction in this high-frequency noise, which significantly improves the signal-to-noise ratio during biomolecule sensing at high bandwidth. This is illustrated in FIG. 8A, where both 5-channel devices (with and without micro-vias) are compared to a nanopore chip mounted in between fluidic reservoirs in a standard macrofluidic cell. In this high frequency range, the 5-channel microfluidic device (without the micro-via) exhibits comparable noise characteristics compared to those acquired in the macroscopic cell. This result is consistent with the argument that noise in this regime arises from the amount of exposed membrane area calculated to be ~3×105 µm2 for the macroscopic reservoir and ~2×105 µm2 for a microchannel in the standard 5-channel device. However, when the exposed membrane area is reduced 350-fold to ~6×102 µm2 using the smallest micro-via (40×15-µm2) of the 5-channel device, high frequency noise is significantly reduced. This noise reduction is further highlighted by the baseline ionic current traces of each device while no voltage applied shown in FIG. 8B, where the peak-to-peak noise at 100 kHz bandwidth is reduced by a factor of 2 (5 at 10 kHz bandwidth) in the configuration with micro-vias, while the RMS noise is reduced by a factor of 7 at 10 kHz and 2 at 100 kHz bandwidth.

With reference to FIGS. 9A and 9B, the functionality of these devices was assessed by observing the translocation of biomolecules. In each case, nanopores were first fabricated and enlarged to a desired diameter as described above. Following sample introduction, flow was minimized in the microfluidic channels by turning off the pressure regulators. FIG. 9A shows a scatter plot of the conductance blockages and durations as individual human α-thrombin (Haematological Technologies, Inc.) molecules at 250 µM concentration are detected using a 10.5-nm nanopore in a microfluidic channel (without vias) in 1 M KCl pH 8.0. Here, protein molecules were loaded in one of the five independent top microfluidic channels, which was biased at −200 mV relative to the grounded common bottom channel. Overall, over 5,000 individual events were observed. FIG. 9B shows a similar scatter plot of DNA translocation events through a different 11.5-nm nanopore, which was localized within a microchannel that included a micro-via. Here, a 3 pM solution of 10-kbp dsDNA in 2 M KCl pH 10 was added to the top microchannel while −200 mV, −250 mV and −300 mV biases were applied relative to the common channel, resulting in over 1,500 translocation events. It is worth noting that the magnitudes of the conductance blockages obtained for both protein and single-level dsDNA events, are in agreement with previously reported models and experiments utilizing standard macrofluidic cells.

The microfluidic design must be considered carefully when integrating nanopores using this approach. While nanopores integrated within microfluidic channels placed directly on the membrane (without a micro-via) were able to capture and detect proteinaceous samples in 30% of the devices tested (9 out of 30), the capture efficiency and experimental yield of devices capable of demonstrating nucleic acid translocation were markedly reduced. Here, the criteria used to defined experimental yield is a device capable of detecting more than 1000 biomolecular translocation events. It is important to note that the placement of the electrodes inside microfluidic channels leading to the membrane introduces non-uniformity in the electric field at the membrane and near the nanopore when the top microchannel contains only a single electrode. It is possible that this asymmetry results in the fabrication of a nanopore near the edge of the membrane (near the edge of the silicon support chip), a region that may be more stressed upon bonding to the PDMS microchannel layer. In this region, the surface charge characteristics of the membrane in the vicinity of the nanopore may electrostatically prevent the translocation of large, highly charged nucleic acid polymers while allowing the passage of less-charged polypeptides. The introduction of a micro-via, however, localizes nanopore fabrication to an intended region in the center of the membrane or away from the edges and ensures a more symmetrical electric field, yield to 3 out of 4 devices tested in pH 10. It is also possible to reduce this asymmetry in the electric field by incorporating pairs of electrodes biased at the same potential, in the top independent channels on either side of the membrane as described above. In this configuration, 5 out of 6 devices tested in pH 8 were successful in detecting at least 1000 biomolecular translocation events.

In yet another aspect of this disclosure, micro valves technology can play a role in achieving microfluidic large scale integration. Development of functionally reliable microvalves is also an important step toward successful miniaturization and commercialization of fully automated microfluidic systems. Microvalves are used to control fluid flow and route the electrical/ionic current throughout the microfluidic network. Various approaches such as screw, pneumatic and solenoid valves can be used to integrate valves within microfluidic devices.

FIG. 11 depicts an example embodiment of the apparatus 110 which employs pneumatic microvalve technology. The apparatus is comprised generally of a top substrate, a bottom substrate, a support structure disposed between the top and bottom substrates, and can also include an intermediate via layer, as described in the embodiments set forth above. In this example embodiment, five microfluidic channels 112 are formed in the top substrate. Again, more or less microfluidic channels can be formed in other embodiments.

The microfluidic channels 112 are routed adjacent to the membrane in a manner that creates an electric field that is uniform across the area of the membrane. For example, each microfluidic channel 112 forms a loop downstream from an electrode 116 where a section of the loop is routed over the membrane. Different closed loop arrangements that bring the electric field lines from two opposing side of the membrane also fall within the scope of this disclosure.

Control valves 114 are also disposed in the microfluidic channels 112 and operate to control the electrically conductive pathway defined by the open or closed valves within the channels. In an example embodiment, the microfluidic channels 112 are embedded within an elastomeric polymer to achieve pneumatic microvalves. These valves are typically fabricated in two layers by using soft lithography techniques. With reference to FIGS. 10A and 10B, the valve is composed of two layers, which are separated with a very thin layer of membrane as indicated at 108 in FIG. 10A. One layer (flow layer) 106 has channels to flow fluids. The separating thin membrane deflects in to the microfluidic channel when control channels (valves) in the other layer (control layer) 107 are pressurized by air or water as seen in FIG. 10B. This will stop the fluid (liquid electrolyte) flow and consequently a seal can be obtained. The amount by which a flow channel is closed is related to the electrical impedance that the valve will impose on the electrical network. For example, a completely closed flow channel may have >10 GΩ impedance (the precise value will depend on electrolyte conductivity and valve geometry), effectively isolating this region of the microfluidic network.

Returning to FIG. 11, each of the five microfluidic channels 112 has at least two valves 114 disposed therein, where one valve is disposed on each side of the membrane. Additionally, each valve 114 is fluidly coupled to and actuated by a pneumatic source (not shown). By controlling the degree each groups of valves closes a microfluidic channel 112, the valves 114 can act as variable resistors in a voltage divider. In this way, valves can be used to route electrical potential through selected microfluidic channels to produce an electric field that is uniform along the area of the membrane.

The inclusion of pneumatic microvalves is a practical way to achieve microfluidic large-scale integration. It is a robust method to independently control on-chip, the value of the electrical potential across the membrane in each microchannels with a few number of electrodes. Microvalves act as voltage dividers (providing >10 G$\Omega$ resistance seals in a microchannel) that allow for the precise control of the electric field across various regions of the membrane. This control is essential for the scalability and functionality of devices in that it: grants the ability to address any number of nanopores for fabrication, size control and sensing with a single pair of electrodes positioned somewhere in the fluidic channels on each side of the membrane; can be used to redirect electrical potential to produce a uniform electric field along the length of the membrane in a particular microchannel (an important feature for biomolecular sensing) using a single pair of electrodes; is necessary for array fabrication and sensing in devices containing a common microchannel (a feature required for serial and parallel probing of a single sample using multiple nanopores); allows for rapid exchange of solutions containing various solvents, ionic strengths, pHs or analytes, facilitating fabrication and sensing; and variable fluidic and electrical resistors for on-chip fabrication and biomolecular sensing. It is also noted that retaining of hydrophobicity of the cross section of the valves and the channels is critical to obtain high resistance sealing used in controlling magnitude and uniformity of electric field across the membrane during fabrication and sensing. This is accomplished by chemically treating each layer of the device prior to assembly, eliminating the requirement of plasma treating the membrane to remove contaminants which would leave the valve cross-section hydrophilic.

Controlling these resistive valves can be used to impose specific electric potential conditions at different locations within the microfluidic network using a reduced number of electrodes. In this embodiment, a single pair of electrodes may be used. The electrodes 116 are positioned in the microfluidic channels on either side of the membrane (only the top electrode is shown in FIG. 11 but a bottom electrode is similarly position below the membrane). Except for the difference described above, the apparatus 110 is similar to the apparatus described in relation to FIG. 2A.

FIGS. 12 and 13 depict other example embodiments of apparatus which employs pneumatic microvalve technology. In FIG. 12, the apparatus 120 is similar to apparatus 110 but further includes a routing valve 121 and a second top electrode 116. During operation, the routing valve 121 remains closed, so that the ionic solution flows through the channels towards the membrane 12 from both the right and left side of the membrane as seen in the figure. The routing valve 121 in effect creates two microfluidic subsystems. One electrode is placed upstream from where the channel divides into five separate microfluidic channels in each of the two microfluidic subsystems.

FIG. 13 depicts a similar apparatus 130 but having only two microfluidic channels 112. Likewise, the two top electrodes are positioned on each side of the membrane and the two microfluidic channels pass over a portion of the membrane. Two control valves 114 are disposed in each microfluidic channel 112, one upstream of the membrane and one downstream of the membrane. Except for the difference described above, these two apparatuses 120, 130 are similar to the apparatus described in relation to FIG. 11.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. An apparatus for fabricating one or more nanopores in a membrane, comprising:
a first substrate having a common microchannel formed in an exposed surface of the first substrate, wherein the membrane is disposed onto the exposed surface of the first substrate and defines opposing planar surfaces;
a second substrate having one or more microfluidic channels formed in an inner surface of the second substrate, the second substrate being disposed onto the membrane with the inner surface facing the membrane such that the one or more microfluidic channels are fluidly separated by the membrane from the common microchannel;
a set of electrodes positioned on opposing sides of the membrane and operate to generate an electric potential across the membrane, wherein the one or more microfluidic channels are routed adjacent to the membrane and configured in a manner that creates an electric field across the area of the membrane that is symmetric with respect to a plane that is perpendicular to the planar surfaces of the membrane.

2. The apparatus of claim 1 wherein a first electrode in the set of electrodes is disposed in the one or more microfluidic channels and the one or more microfluidic channels form a loop downstream from the electrode where a section of the loop is routed over the membrane.

3. The apparatus of claim 1 wherein the one or more microfluidic channel are further defined as a plurality of microfluidic channels routed over the membrane, and the plurality of microfluidic channel are arranged symmetrical in relation to each other in an area adjacent to the membrane.

4. The apparatus of claim 3 where the microfluidic channels are substantially straight and parallel with each other in an area adjacent to the membrane.

5. The apparatus of claim 1 further comprises a control valve disposed in the one or more microfluidics channel and operate to control amount of fluid flow through the one or more microfluidic channels.

6. The apparatus of claim 1 further comprises a control valve disposed in the one or more microfluidics channel and operate to control amount of electric current flow through the one or more microfluidic channels.

7. The apparatus of claim 5 wherein the control valve is further defined as an elastomeric polymer fluidly coupled to and actuated by a pneumatic source.

8. The apparatus of claim 1 wherein the second substrate includes an array of microfluidic channels formed in the inner surface thereof, where each microfluidic channel in the array of microfluidic channels passes over a portion of the membrane and has at least two control valves disposed therein, one valve is disposed upstream of the membrane and the other value disposed downstream of the membrane.

9. The apparatus of claim 1 further comprises
a current sensor electrically coupled to one of the electrodes in the set of electrodes and operable to measure current flowing between one of the one or more microfluidic channels and the common microchannel; and
a controller interfaced with the current sensor, wherein the controller detects an abrupt increase in the measured current which indicates formation of a pore through the membrane and, in response to detecting the abrupt increase in the measured current, removes the electric potential applied across the membrane.

10. The apparatus of claim 1 wherein the one or more microfluidic channels have dimension on the order of microns.

11. The apparatus of claim 1 wherein the one or more microfluidic channels have dimension on the order of nanometers.

12. An apparatus for fabricating one or more nanopores in a membrane, where the membrane defines opposing planar surfaces and is comprised of at least one dielectric layer, comprising:
a first substrate having a common microchannel formed in an exposed surface of the first substrate;
a support structure disposed onto the exposed surface of the first substrate and configured to host a membrane;
a second substrate having one or more microfluidic channels formed in an inner surface of the second substrate, the second substrate being disposed onto the support structure with the inner surface facing the support structure such that the one or more microfluidic channels are fluidly separated by the membrane from the common microchannel;
a pair of electrodes arranged on opposing sides of the membrane, wherein the pair of electrodes generates an electric potential across the membrane, wherein the one or more microfluidic channels are routed adjacent to the membrane and configured in a manner that creates an electric field across the area of the membrane that is symmetric with respect to a plane that is perpendicular to the planar surfaces of the membrane.

13. The apparatus of claim 12 wherein the one of the pair of electrode is disposed in the one or more microfluidic channels and the one or more microfluidic channel forms a loop downstream from the electrode where a section of the loop is routed over the membrane.

14. The apparatus of claim 12 wherein the one or more microfluidic channel is further defined as a plurality of microfluidic channels routed over the membrane, where the microfluidic channel are substantially straight and parallel with each other in an area adjacent to the membrane.

15. The apparatus of claim 12 further comprises a control valve disposed in the one or more microfluidics channel and operate to control amount of fluid flow through the one or more microfluidic channels.

16. The apparatus of claim 12 further comprises a control valve disposed in the one or more microfluidics channel and operate to control amount of electric current flow through the one or more microfluidic channels.

17. The apparatus of claim 16 wherein the control valve is further defined as an elastomeric polymer fluidly coupled to and actuated by a pneumatic source.

18. The apparatus of claim 12 wherein the second substrate includes an array of microfluidic channels formed in the inner surface thereof, where each microfluidic channel in the array of microfluidic channels passes over a portion of the membrane and has at least two control valves disposed therein, one valve is disposed upstream of the membrane and the other value disposed downstream of the membrane.

19. The apparatus of claim 12 further comprises
a current sensor electrically coupled to one of the electrodes and operable to measure current flowing between one of the one or more microfluidic channels and the common microchannel; and
a controller interfaced with the current sensor, wherein the controller detects an abrupt increase in the measured current which indicates formation of a pore through the membrane and, in response to detecting the abrupt increase in the measured current, removes the electric potential applied across the membrane.

20. The apparatus of claim 12 wherein the one or more microfluidic channels have dimension on the order of microns.

21. The apparatus of claim 12 wherein the one or more microfluidic channels have dimension on the order of nanometers.

* * * * *